(12) United States Patent
Alsbou

(10) Patent No.: US 10,912,509 B2
(45) Date of Patent: Feb. 9, 2021

(54) PORTABLE INTELLIGENT DRIVER'S HEALTH MONITORING SYSTEM FOR SAFETY ON THE ROAD

(71) Applicant: UNIVERSITY OF CENTRAL OKLAHOMA, Edmond, OK (US)

(72) Inventor: Nesreen Alsbou, Edmond, OK (US)

(73) Assignee: UNIVERSITY OF CENTRAL OKLAHOMA, Edmond, OK (US)

( * ) Notice: Subject to any disclaimer, the term of this patent is extended or adjusted under 35 U.S.C. 154(b) by 0 days.

(21) Appl. No.: 16/284,304

(22) Filed: Feb. 25, 2019

(65) Prior Publication Data
US 2020/0268301 A1 Aug. 27, 2020

(51) Int. Cl.
| | |
|---|---|
| *A61B 5/18* | (2006.01) |
| *G07C 5/08* | (2006.01) |
| *G07C 5/00* | (2006.01) |
| *B60Q 9/00* | (2006.01) |
| *H04W 4/46* | (2018.01) |

(Continued)

(52) U.S. Cl.
CPC ............ *A61B 5/18* (2013.01); *A61B 5/024* (2013.01); *A61B 5/6893* (2013.01); *A61B 5/742* (2013.01); *A61B 5/746* (2013.01); *A61B 5/7455* (2013.01); *B60Q 9/00* (2013.01); *G07C 5/008* (2013.01);

(Continued)

(58) Field of Classification Search
CPC ......... A61B 5/18; A61B 5/024; A61B 5/6893; A61B 5/742; A61B 5/7455; A61B 5/746; H04W 4/46; B60Q 9/00; G07C 5/008; G07C 5/0825; G07C 5/085
See application file for complete search history.

(56) References Cited

U.S. PATENT DOCUMENTS

| | | | |
|---|---|---|---|
| 8,725,311 B1 | 5/2014 | Breed | |
| 8,847,771 B2 | 9/2014 | Gunaratne et al. | |
| 9,402,577 B2 | 8/2016 | Ko et al. | |
| 2016/0001781 A1* | 1/2016 | Fung | G16H 50/20 |
| | | | 701/36 |
| 2017/0200061 A1* | 7/2017 | Julian | G08G 1/04 |

(Continued)

OTHER PUBLICATIONS

T. Hu, "A Framework of Truck Overload Intelligent Monitoring System," 2011 Fourth International Symposium on Computational Intelligence and Design, Hangzhou, 2011, pp. 107-110. DOI: 10.1109/ISCID.2011.128.

(Continued)

*Primary Examiner* — Sisay Yacob
(74) *Attorney, Agent, or Firm* — Berenato & White, LLC

(57) ABSTRACT

A system and method for detecting abnormal motor vehicle operation and providing notification and alerts to third parties, comprising: an impediment proximity detection subsystem including sensors at least mounted at external surfaces of said vehicle, said impediments consisting of at least fixed and moving objects external to said vehicle; a vital sign detection subsystem installed in said vehicle, including driver monitoring sensors and providing a measure of at least driver pulse rate and hand location; a controller installed in said vehicle, for receiving and processing sensor produced signals; an alarm subsystem installed in said vehicle, producing at least one of a visual or vibrational signal; a cloud interface subsystem including at least a WiFi transceiver installed in said vehicle, and a Google Cloud IoT Service or equivalent, and a vehicle to vehicle communication subsystem installed in said vehicle, using the BroadR-Reach® standard for automotive Ethernet or its evolving equivalents.

15 Claims, 14 Drawing Sheets

(51) Int. Cl.
*A61B 5/024* (2006.01)
*A61B 5/00* (2006.01)

(52) U.S. Cl.
CPC ........... *G07C 5/085* (2013.01); *G07C 5/0825* (2013.01); *H04W 4/46* (2018.02)

(56) References Cited

U.S. PATENT DOCUMENTS

| | | | |
|---|---|---|---|
| 2017/0270788 A1* | 9/2017 | Cain | G08G 1/0141 |
| 2017/0278323 A1* | 9/2017 | Gupta | H04W 64/00 |
| 2017/0355377 A1* | 12/2017 | Vijaya Kumar | B60C 9/0007 |
| 2017/0368893 A1* | 12/2017 | Kodama | H04N 21/43637 |

OTHER PUBLICATIONS

L. Marantis, A. Paraskevopoulos, D. Rongas, A. Kanatas, C. Oikonomopoulos-Zachos and S. Voell, "A printed monopole ESPAR antenna for Truck-to-Truck communications," 2017 International Workshop on Antenna Technology: Small Antennas, Innovative Structures, and Applications (iWAT), Athens, 2017, pp. 239-242. DOI: 10.1109/IWAT.2017.7915368.

J. Klimke, P. Themann, C. Klas and L. Eckstein, "Definition of an embedded driver model for driving behavior prediction within the DESERVE platform," 2014 International Conference on Embedded Computer Systems Architectures, Modeling, and Simulation (SAMOS XIV), Agios Konstantinos, 2014, pp. 343-350. DOI: 10.1109/SAMOS.2014.6893231.

M. A. Al-Abed, M. Manry, J. R. Burk, E. A. Lucas and K. Behbehani, "Sleep disordered breathing detection using heart rate variability and R-peak envelope spectrogram," 2009 Annual International Conference of the IEEE Engineering in Medicine and Biology Society, Minneapolis, MN, 2009, pp. 7106-7109. DOI: 10.1109/IEMBS.2009.5332897.

* cited by examiner

PORTABLE INTELLIGENT DRIVER'S HEALTH MONITORING SYSTEM FOR SAFETY ON THE ROAD

STATEMENT AS TO RIGHTS TO INVENTIONS MADE UNDER FEDERALLY SPONSORED RESEARCH OR DEVELOPMENT

Not applicable.

FIELD OF THE INVENTION

The present invention generally relates to safe operation of a motor vehicle and methods for monitoring thereof. More specifically, the present invention relates to a detection system and method for monitoring a driver operating a motor vehicle, particularly as to a driver's behavior and health condition and reacting to thereto.

BACKGROUND OF THE INVENTION

The majority of traffic accidents involving trucks are the result of personal factors affecting drivers, such as driving habits, attention deficit, fatigue or health condition. Many driving safety systems respond only to the abnormal driver himself or the abnormal driving behavior. These systems include LDWS (Lane Departure Warning System), FCW (Forward Collision Warning), and AES (Autonomous Emergency System).

A few systems are directed to monitoring the physiological status of a driver, particularly a driver's personal fatigue. Such systems may attempt to gage the physiological status of a driver according to a single standard. A failing of single standard status determination is the tendency to over-respond or under-respond to deviant operation, which may endanger the driver and other proximate vehicles. One attempt to address these problems is disclosed by Ming-Kuan Ko, et al. (U.S. Pat. No. 9,402,577B2), which provides a driver's fatigue detection system and method that uses a plurality of sensors to detect the status of a driver from different aspects, whereby to detect the physiological status of the driver more accurately. The system disclosed by Ko et al. in the '577 patent comprises a vital sign detection device generating at least one personal vital sign value; a storage device storing a linear statistic equation; a processor electrically connected with the vital sign detection device and the storage device; and a display device electrically connected with the processor. The processor receives the personal vital sign value, retrieves the linear statistic equation, substitutes the personal vital sign value into the linear statistic equation to generate a predictive vehicle deviation value, and determines whether the predictive vehicle deviation value is over a preset vehicle deviation value. If yes, the processor generates an alert signal to the display device to present an alert image to the driver. The invention disclosed determines whether the stability of the driver is decreasing according to his physiological status and reminds the driver to avoid a traffic accident beforehand.

Another attempt to address these problems is disclosed by David Breed (U.S. Pat. No. 8,725,311B1), which provides a driver health and fatigue monitoring system that includes sets of electric field antennas integrated into a vehicle seat, each including at least one antenna, a control unit connected to the antenna sets and including selectors coupled to the antennas. The selectors are controlled by the control unit to obtain signals from one or more antennas serving as receiving antennas and one or more antennas serving as sending antennas. The control unit determines which combination of sending antenna(s) and receiving antenna(s) provides a strongest signal in an expected heartbeat range and/or expected respiration range of the seat occupant, then monitors this combination for changes and/or deviations from a normal range of heartbeats and/or respiration. Changes and/or deviations from the normal range of heartbeats and respiration rate are used to assess drowsiness or sleepiness of the seat occupant, especially the driver of the vehicle, and activate a notification system that requires a response to enable continued operation of the vehicle by the driver.

In U.S. Pat. No. 8,847,771B2, Pujitha Gunaratne, et al. disclose a method and apparatus for determining an inattentive state of an operator of a vehicle and for providing information to the operator of the vehicle by obtaining face images of the operator of the vehicle, obtaining images of an environment of the vehicle, determining one or more areas of interest in the environment of the vehicle based on the images of the environment, obtaining, from a relevance and priority database, relevance and priority values corresponding to the one or more areas of interest, determining a probability of attention of the operator of the vehicle to the one or more areas of interest based on the images of the environment and the relevance and priority values, determining an attention deficiency based on the determined probability of attention and the face images, and providing the information to the operator of the vehicle based on the determined attention deficiency.

The forgoing examples are representative of the related art which is generally directed to systems for monitoring the attention, fatigue and/or health status of a driver while operating a motor vehicle. Corrective action in response to degraded or deviant operation from a standard or norm is primarily an alert or notification intended to prompt corrective action by the driver or by an automated control present in the vehicle. While attention, health status, or fatigue assessment may be a part of such driver monitoring systems and provide alerts to a vehicle's driver, none provide notifications to a centralized authority (e.g., truck fleet operator) and alerts to surrounding vehicles intended to prompt avoidance of a vehicle operated by a driver experiencing a health or fatigue related event. Accordingly, the present invention provides a system and method to solve the abovementioned problems.

SUMMARY OF THE INVENTION

According to a preferred embodiment of the present invention, a system and method is provided for monitoring the attention, health status, and operating behavior of a driver operating a motor vehicle (e.g., commercial trucks, automobile), and in the event of degraded operation of said motor vehicle by the driver, notification or alerts are communicated to third parties. The present invention is unique at least for the reason that it monitors the health condition and fatigue level of a driver operating a specific vehicle and alerts surrounding vehicles to avoid that specific vehicle in the event of a health or fatigue related negative event. While different passenger automobile (i.e., car) models have "smart" technologies imbedded in them to monitor a driver's operational behavior, trucks used for commercial purposes have none to minimal technologies implemented in them. Presently available systems for automobiles and commercial trucks do not provide notifications or alerts to third parties in the event of abnormal operation of a vehicle. The present invention is particularly relevant to commercial trucking companies because the drivers and operating vehicles stay on the road for long periods and currently no such monitoring system exists. However, use of the present invention is not limited to commercial trucks. The system and method provided by the present invention can also be used in private automotive vehicles (i.e., cars/trucks). The system is portable and adjustable and can be configured to fit any car or truck. In addition, the health monitoring system is configurable to monitor specific signs associated with the driver health conditions, such as diabetic, high blood pressure, or heart irregularities, as well as fatigue profiles for a specific driver.

Accidents involving large commercial trucks can be prevented if the driver's health is monitored and corrective action taken. For example, if the driver's pulse is monitored, lower pulse rate is an indication of possible problems and may cause lower concentration. The driver's vital signs can be monitored to keep track of his health and well-being over time. If the driver is driving with only one or no hands on the wheel because of fatigue or texting, the system provided by the present invention can also detect that behavior, as well as all of the forgoing signs and indications. Key components of the apparatus of the present invention include, but are not limited to pulse sensors, pressure sensors, adaptable steering wheel (e.g., JDM Black Leather steering wheel), FLORA—Wearable Micro-Controller. The pulse sensor (e.g., MAX30102) is used to measure heart rate. This can be done by measuring the time between the pulses. The pulse sensor output can be filtered and amplified. A pressure sensor (e.g, Extra-long force-sensitive resistor (FSR)—Interlink 408) may be used to detect the presence of the driver's hands on the steering wheel. The output of the pressure sensor is also amplified. Proximity sensors (e.g., Ultrasound, Microwave, LIDAR) may be used for collecting relative positioning data. Proximity sensors such as Ultrasound Sensor: Maxbotix Ultrasonic Rangefinder—LV-EZ1-LV-EZ1, and Microwave Sensor: HB100 and LIDAR Sensor: LIDAR-Lite v3-SEN-14032 may be mounted on the front and the sides of the vehicle to detect the presence of fixed or dynamic impediments (e.g. guard rails, automobiles). Both the pulse sensor and the pressure sensor, as well as the proximity sensors, are controlled by microcontroller (e.g., FLORA microcontroller) which is adapted to be installed behind an airbag if present in a steering wheel. The microcontroller may also be located on or within the dashboard of a vehicle. The driver alert subsystem may provide a visible or vibrating alarm or both. The driver alert subsystem may incorporate both visual (e.g., LED) and physical stimulators (e.g. vibrators). In the event the data collected by the sensors and analyzed by the microcontroller points to a dangerous situation, as an alert to the driver, the microcontroller will activate at least one physical stimulator, and illuminate an LED. A notification will be will be transmitted to third parties.

The foregoing paragraphs provide a general introduction, and are not intended to limit the scope of the claims presented herein. The described embodiments, together with further advantages, are best understood by reference to the following detailed description taken in conjunction with the drawings presented. Below, the embodiments as described in detail will make easily understood the objectives, technical contents, characteristics and accomplishments of the present invention.

DETAILED DESCRIPTION OF THE INVENTION

In Brief: in one embodiment, data readings of the health and operational behavior of the driver are captured absent wiring attached to his body, avoiding physical discomfort or constraint while driving. Most readings may be taken from the steering wheel. An optical sensor may be used for reading the driver body motion. Other sensor types may also be incorporated into the system, and are anticipated as sensor technology evolves.

In one embodiment, situational data collected by the monitor subsystem, specific to the driver and vehicle being operated, will be automatically and wirelessly transmitted through the cloud as a message to an appropriate third party recipient. Data transmission may be accomplished using a WiFi Transceiver and an interface to a cloud communication service such as Google Cloud IoT Service or Ubidots Cloud Service. An equivalent service may be utilized comprising scalable, fully-managed cloud services. A user-interface for receiving and accessing event data is included.

In one embodiment, the system provided by the present invention provides the capabilities to receive and process data from all system components, including the sensors. The data may be transmitted using a 4g/LTE process or similar means (and as communication methods may evolve) to the cloud and stored in a cloud services account for the third party (e.g., commercial trucking company) to monitor. Any detected abnormalities in the data collected prompts a message to be sent to the third party and as an alert to the driver.

In one embodiment, the system provided by the present invention uses at least vehicle to vehicle communication enabled for example by the BroadR-Reach® standard for automotive Ethernet or its evolving equivalents to spread warning messages to surrounding vehicles alerting their drivers to avoid a specific vehicle (e.g., a commercial truck) experiencing abnormal operation.

In one embodiment, visual alerts (e.g., flashing lights, signal messages) may also be provided on alert displays mounted on the exterior of a vehicle configured with the system of the present invention.

In one embodiment, the present invention provides a method for delivering timely alerts and notification of abnormal operation of a specific vehicle to third parties at interest (e.g., commercial trucking company, fleet managers) as commercial vehicle operators.

In one embodiment, the present invention provides a method for delivering timely alerts and notification of abnormal operation of a specific vehicle to drivers in surrounding vehicles.

Figure 1:
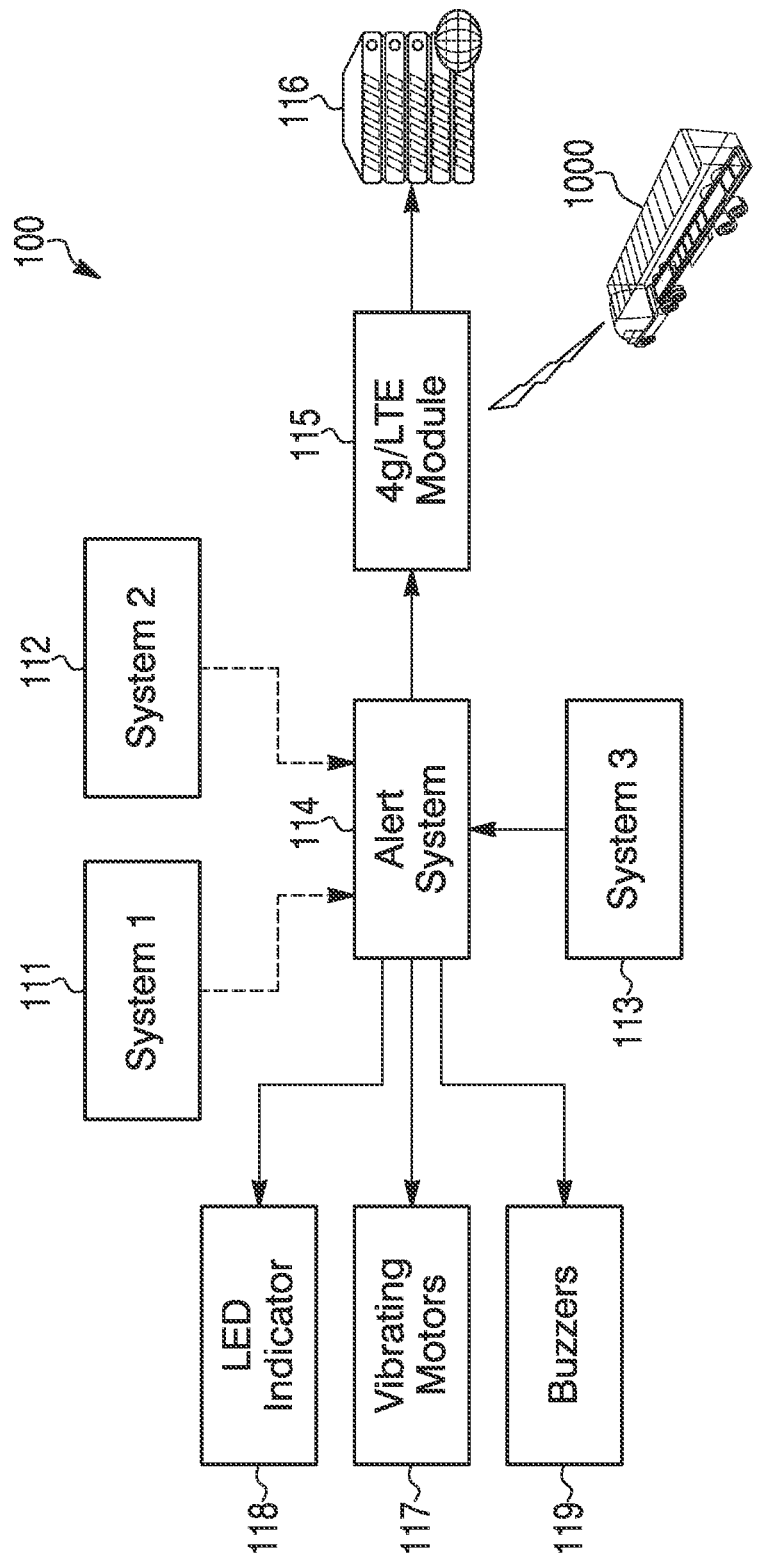
FIG. 1 is a non-limiting diagram schematically showing the elements comprising the system according to embodiments of the present invention.
Figure 2:
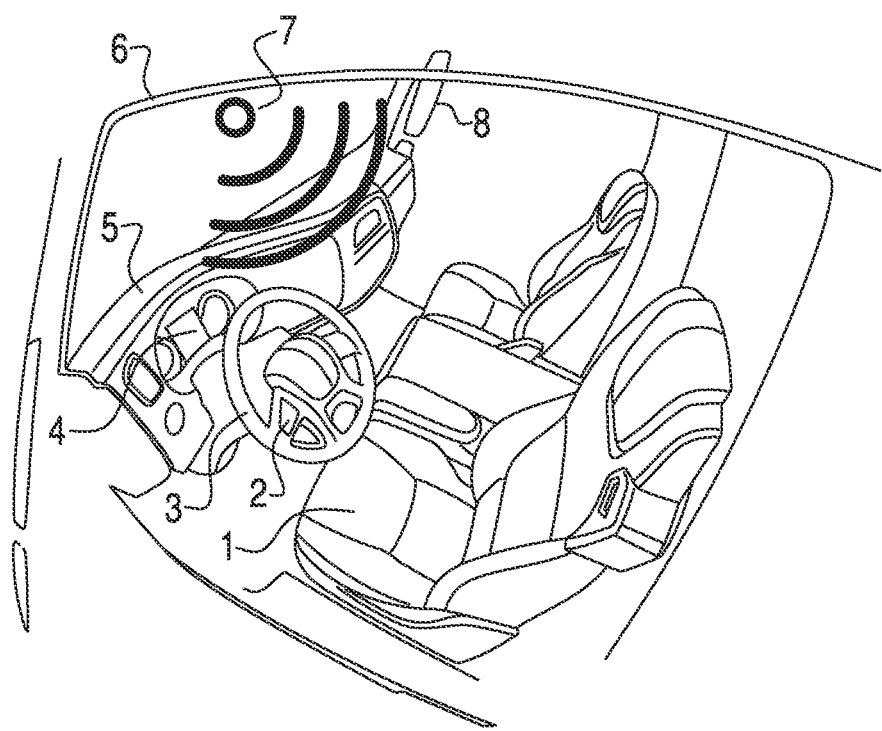
FIG. 2 is a non-limiting diagram showing an exemplary placement of system components in a cab of a commercial truck.

In Detail: referring now to FIG. 1 a non-limiting diagram schematically shows elements comprising the system according to a preferred embodiment of the present invention. The portable health monitoring system 100 includes vital sign sensors 111 that may include pulse sensors that measure heart rate determined for example by measuring the time between the pulses. Vital sign sensors 111 may also include microwave sensors used to measure the driver's lung function (i.e., breathing rate) as well. The output of vital sign sensors 111 may be filtered and amplified. Pressure sensors 112 are implemented in order to detect whether the driver is holding his/her hand on the steering wheel of a motor vehicle. The output of pressure sensors 112 may also be amplified. Both types of sensors (vital sign 111 and pressure 112) are controlled by a microcontroller 113 (e.g., FLORA) which may be placed behind an airbag in the vehicle steering wheel, mounted on the dashboard, or located elsewhere in the cab of a vehicle (FIG. 2).

When the readings from the system sensors 111 and 112 are at a dangerous level, an alarm signal will be sent by the alert system 114 to the driver as notification of the situation and to stimulate appropriate corrective action. The signal will be sent by the alert system 114 to the cloud using a communication module 115 (e.g., WiFi Transceiver or 4g/LTE) and an interface to a cloud communication service 116 such as Google Cloud IoT Service to be processed. The company headquarters (not shown) will be notified of an adverse event by the cloud service 116. For example, if the driver is detected to be sleepy, a signal will be sent to the microcontroller 113 which will then trigger alert system 114 to activate warning indicators to alert the driver and wake him up, the indicators including any of a vibrating motor 117, LED indicator 118, or buzzers 119.

In a preferred embodiment, a web application designed using Ubidots or similar application may be used to provide communication connection between the driver (not shown), the truck (FIG. 2), and the company headquarters (not shown) through the cloud service 116. Collected data will be processed at the cloud service 116 and alerts will be displayed and warnings will go out. The data is regularly updated and allowed to be monitored at the trucking company headquarters (not shown) or other operating location. The cloud service 116 used in one preferred embodiment is Google Cloud IoT which provides a complete set of tools to connect, process, store, and analyze data both at the edge and in the cloud. The Google Cloud IoT platform consists of scalable and fully-managed cloud services. The Google Cloud IoT cloud platform will receive and process data from the monitoring system 100. The use of cloud computing will allow for the collected data to be stored, processed and monitored by the trucking company. If there are any abnormalities in the collected data, a message will be delivered to the company as notice and to the driver in order to alert him/her. If there was no immediate response from the driver, appropriate actions will be initiated by the monitoring system 100 to prevent/minimize the possibility of accidents, including sending alerts to nearby vehicles (1000).

In one preferred embodiment, the monitoring system 100 may send alerts to nearby automotive vehicles 1000 using vehicle to vehicle communication enabled for example by the BroadR-Reach® standard for automotive Ethernet or its evolving equivalents, alerting their drivers to avoid a specific vehicle (e.g., a commercial truck) exhibiting abnormal operation. Electronic display signage (not shown) may be mounted on external surfaces of a commercial vehicle to provide visual alerts of abnormal operation to drivers in nearby vehicles. A smartphone application may be included to allow for immediate accident notification to the drivers in surrounding trucks, as well as emergency services. Truckers will be notified of any accident location and will be given an alternative route to avoid being stuck in the traffic due to an accident in their area. This feature will save time and money in trucking company operations and will shorten cargo delivery time.

Figure 3:
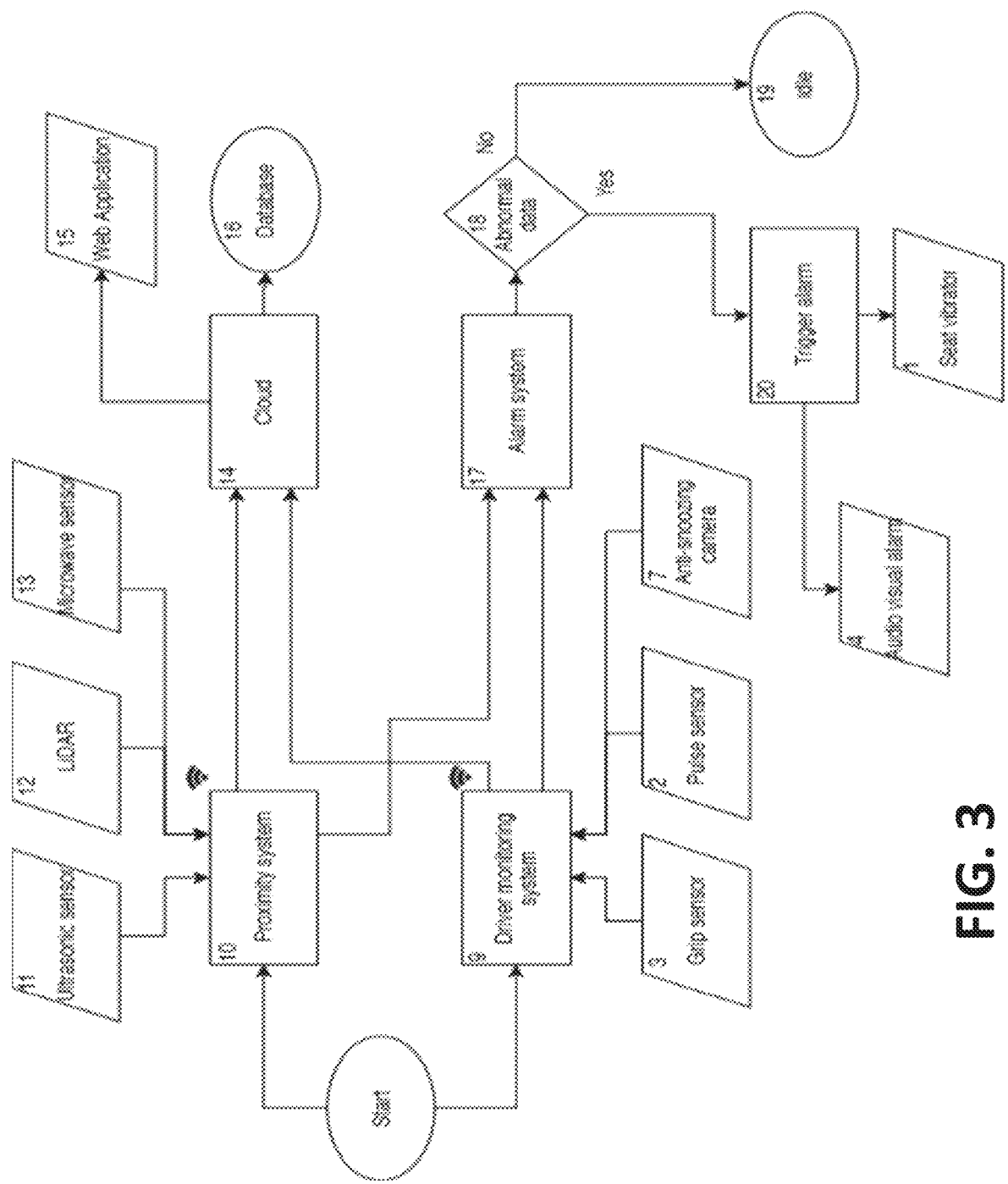
FIG. 3 is a non-limiting diagram showing an overall flowchart of the present invention according to one embodiment.

Referring now to FIG. 2, a non-limiting diagram shows exemplary placement of system components in a cab of a commercial truck, where the semi-truck driver cabin design would include in a preferred embodiment the following:
1—Seat vibrating Alarm
2—Pulse sensors
3—Steering wheel pressure sensors
4—Buzzer, LED warning lights, and LCD alarm display
5—Collision Detection Alarm
6—mm Wave Sensing Solution
7—Anti-Snoozer
8—Blind-spot Detection warning LED Referring now to FIG. 3, a non-limiting diagram shows an overall process flowchart of the present invention according to one embodiment. The driver monitoring subsystem 9 keeps track of the driver behavior and health signs. The most valuable asset inside the truck is the driver him/herself, thus the need to monitor the vital signs of the vehicle operator. Making sure the driver is fit to drive and paying attention can prevent many accidents. The anti-snoozing camera 7 can be used to monitor driver attention. A lot of accidents could be prevented if the driver was simply more rested before hitting the road. Determining if the driver is tired or not can be done by measuring his/her pulse rate using the pulse sensor 2, in addition to the anti-snoozing camera 7. A lower pulse rate is usually associated with lower concentration. It is also important to monitor the driver's vital signs in case he/she might be in need of medical attention. Driver pulse rate as measured by the pulse sensor 2 or other types of sensors including heart rate and lung function sensors (not shown) may be used to monitor vital signs. Moreover, one of the worst behavioral driving habits is to steer with one or no hands on the wheel because of fatigue, texting or other distracting driver activity. This behavior can be detected using the grip sensor 3.

The proximity detection subsystem 10 monitors the operating perimeter of a vehicle to identify impediments to safe operation consisting of at least fixed and moving objects. A LIDAR sensor 12 may be used to measure long range obstacles, collisions, as well breaking detection. The microwave sensor 13 may be used to measure the speed of a front facing vehicle. An ultrasonic sensor 11 may be used to detect blind spots as well as short range obstacles. Abnormal vital signs detected by the driver monitoring subsystem 9 and impediments detected by the proximity subsystem 10 trigger alerts directed to the cloud subsystem 14 and the alarm subsystem 17 to provide notification to third parties of an abnormal operating condition. Parameters outside the normal allowable range trigger an alarm 20 manifested in a physical stimulus using for example a seat vibrator 1 or a sensory stimulus using for example an audio or visual alarm 4. A visual alert may be displayed on electronic signage (not shown) mounted on external surfaces of a vehicle.

Figure 4:
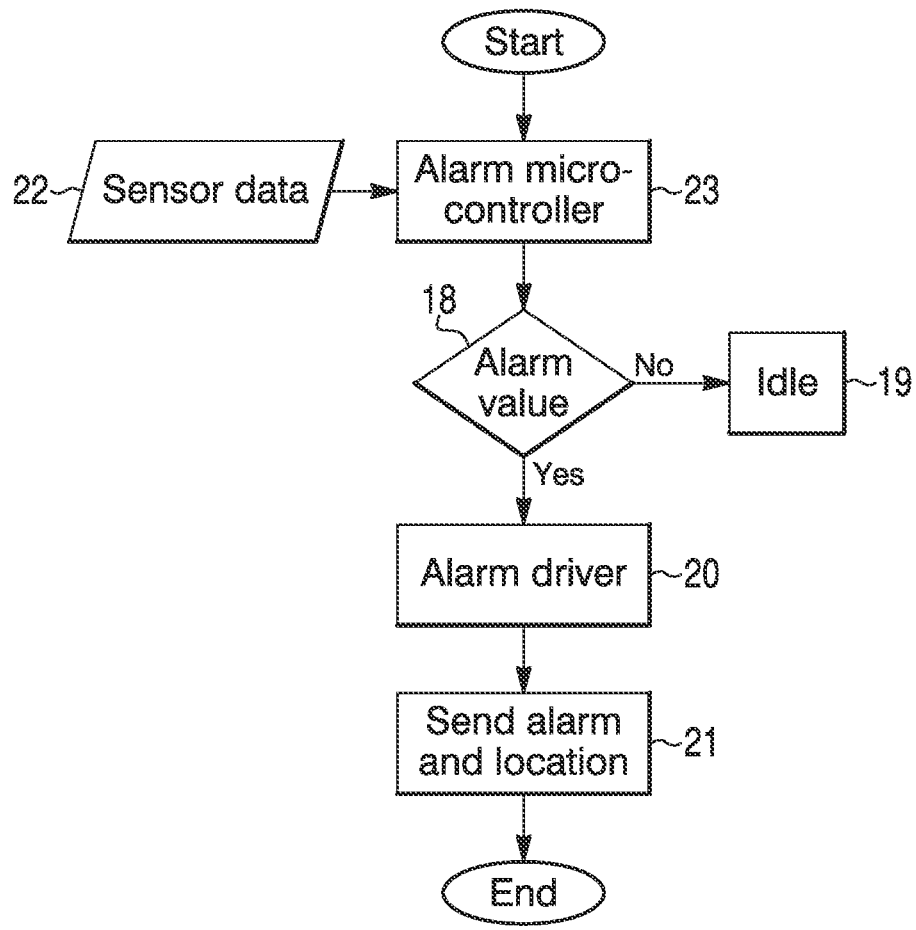
FIG. 4 is a non-limiting diagram showing an exemplary flowchart of the alert and notification process according to one embodiment of the present invention.
Figure 5:
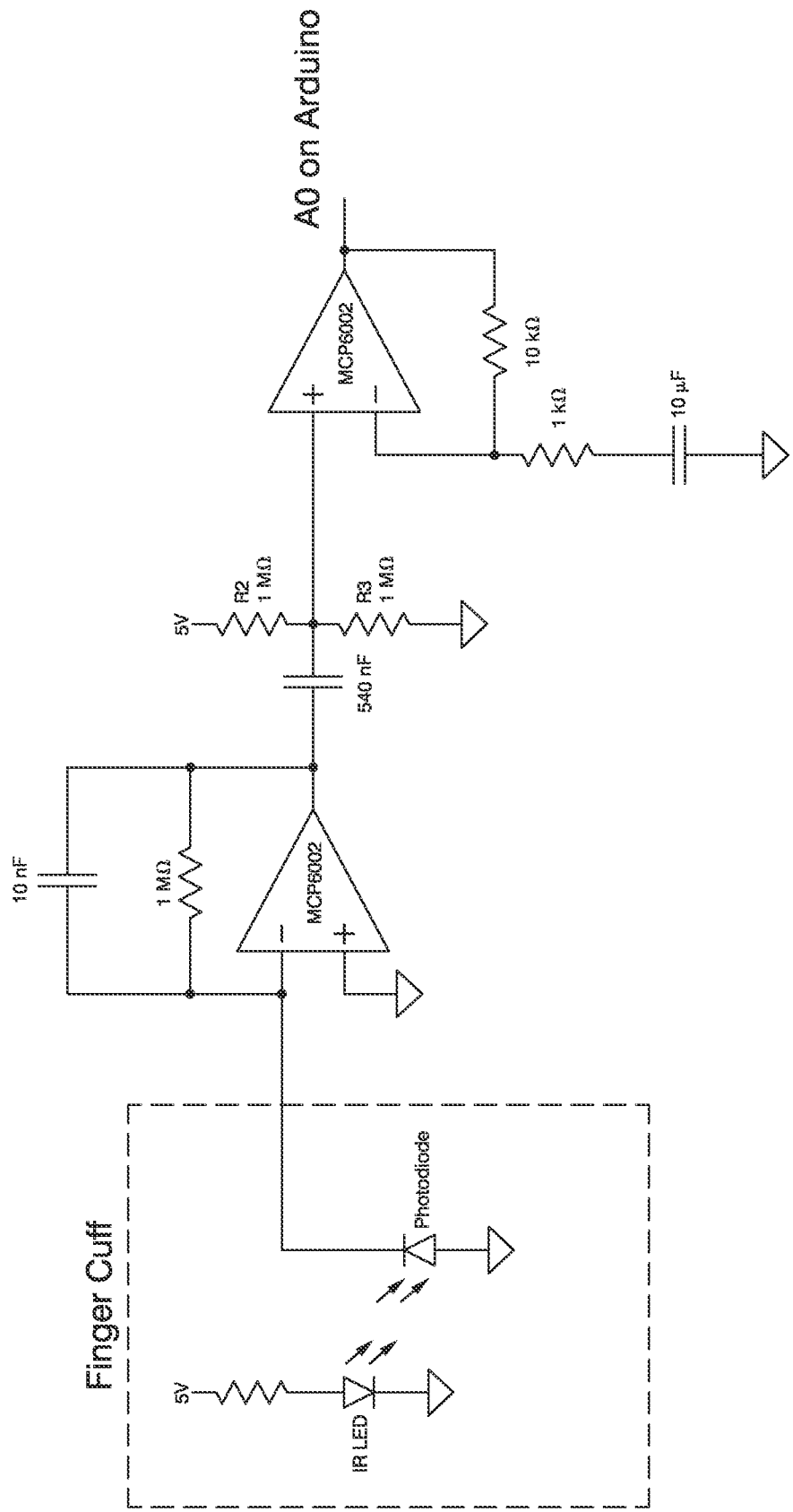
FIG. 5 is a non-limiting diagram schematically showing an exemplary pulse sensor amplification circuit according to one embodiment of the present invention.

Now referring to FIG. 4, a non-limiting diagram shows an exemplary flowchart of the alert and notification process according to one embodiment of the present invention. Sensor data 22 is sent to a micro-controller 23 in the alarm subsystem (FIG. 3-17) which is compared to preset threshold values. If the preset thresholds are not exceeded, no alarm is triggered and an idle state 19 remains. If preset threshold values are exceeded, at least a driver alarm 20 is triggered and an alarm condition is set as any of a physical and sensory stimulus 21, along with capturing the geographic location where the triggering event occurred. Both alarm condition data and event location are sent to the cloud subsystem (FIG. 3-14).

Experimental Aspects

Portable Intelligent Driver's Health Monitoring System Design

A complete prototype system was designed for the purpose of vehicle accident and accident cause prevention. In an operational system, smart IoT technology will be used to collect data from sensors from multiple trucks and add them in a connected loop. This data will be saved in a database (FIG. 3—15) in order to study truck drivers' behavior. Our laboratory research was directed to four primary aspects of the present invention (FIG. 1—100). The first aspect was the driver monitoring subsystem (FIG. 3—9). The driver monitoring subsystem (FIG. 3—9) will be located in the interior of a motor vehicle and will measure vital signs of the driver using a plurality of sensors (e.g., FIG. 3—2, 3, 7). Data indicating the driver vital signs will be processed in order to determine if the driver is in immediate danger or in a life threatening situation. The second aspect was the proximity subsystem (FIG. 3—10) comprising exterior sensors (FIG. 3—11, 12, 13). This system was purposed to detect the distance of vehicles to the front of a tuck as well as their velocity. Another sensor in the proximity subsystem system was purposed to detect long distance crashes. The third aspect was an alarm system (FIG. 3—17) that will sound in the case of a life threatening scenario. This can either be due to abnormal vital signs or due to an accident being detected in the vehicle's vicinity. The fourth aspect was a cloud interface (FIG. 3—14) that will receive, process and transmit data back to the driver and the trucking company. This whole system (FIG. 1—100) will be connected to a smart application that will integrate all this data and send it to the company to monitor their drivers. A user-interface for receiving and accessing event data is included.

Driver Monitoring Subsystem

Materials

The materials used for this subsystem prototype were:
1—Pulse Sensor Optical Heart Rate Monitor (World Famous Electronics, LLC)
2—Pressure Sensor (FlexiForce® by Tekscan)
3—JDM Black Leather Steering wheel (Superb Autoparts)
4—FLORA—Wearable Micro-Controller (Adafruit Industries)

Instrumentation

Simulation for the circuits was accomplished using NI Multisim. Testing and benchmarking was done by constructing the market circuits and obtaining readings using Arduino® software.

Methods

Figure 8:
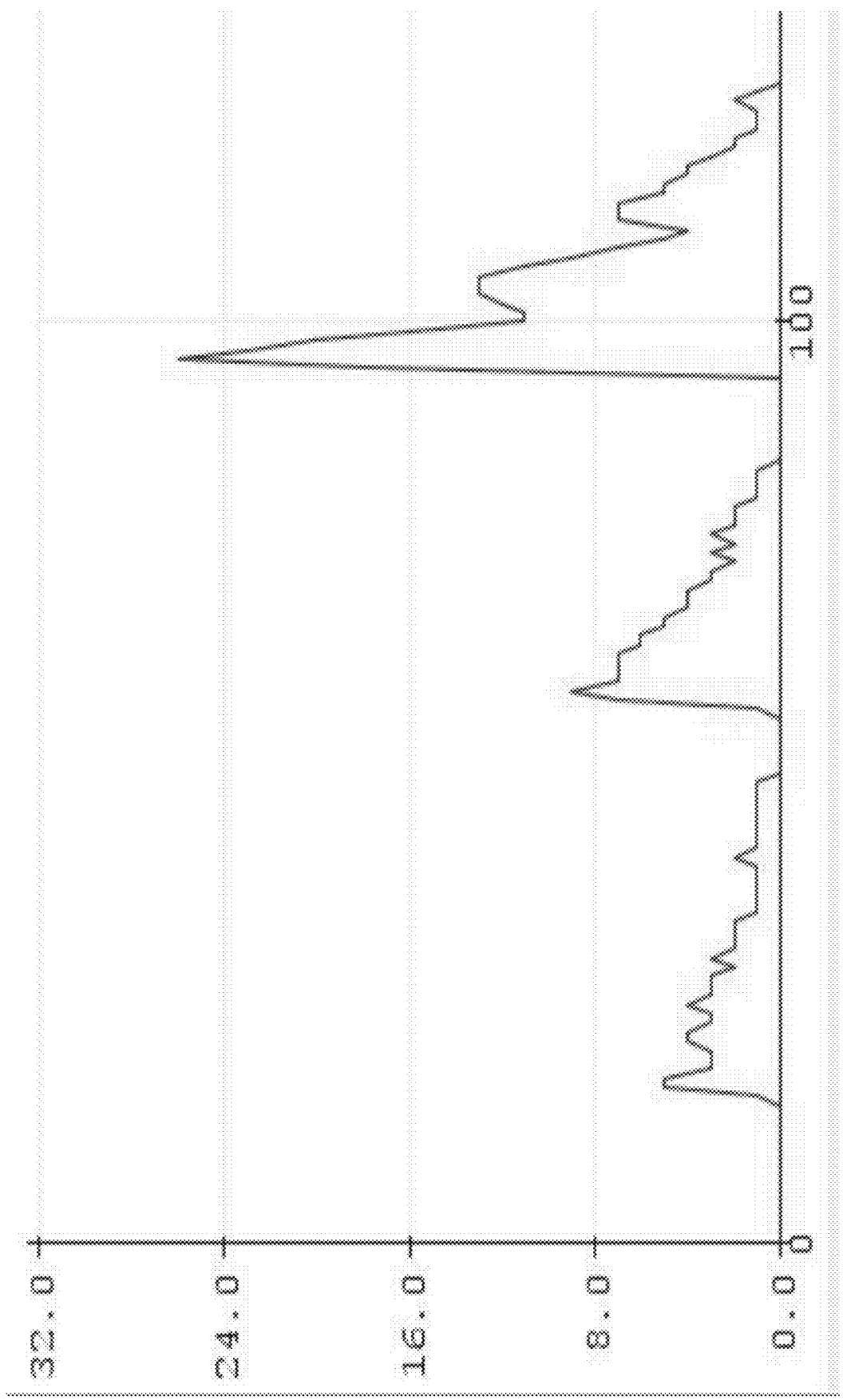
FIG. 8 is a non-limiting diagram showing an exemplary pressure sensor output from the corresponding amplification circuit according to one embodiment of the present invention.
Figure 9:
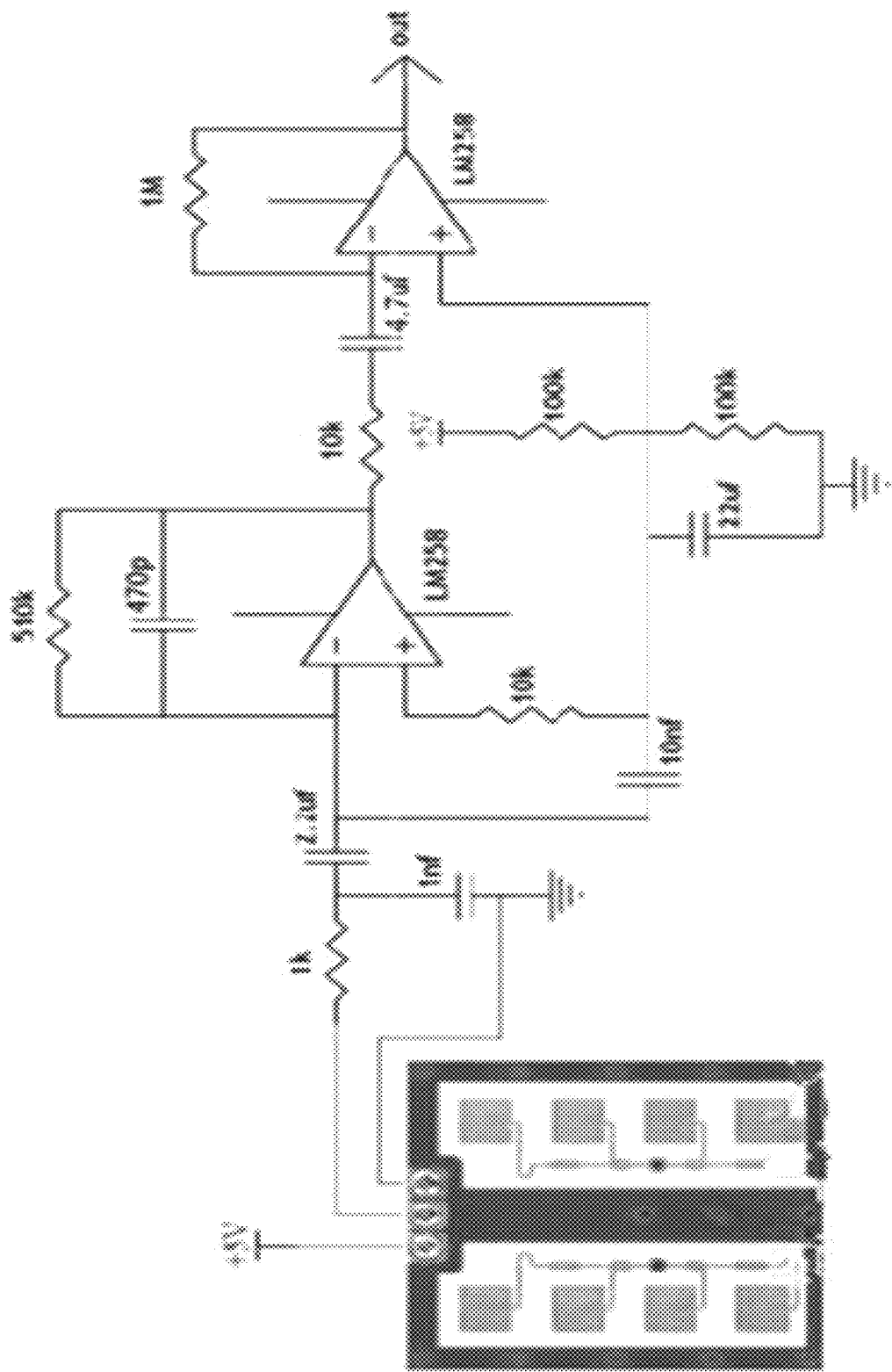
FIG. 9 is a non-limiting diagram schematically showing an exemplary microwave amplification circuit according to one embodiment of the present invention.

The Pulse Sensor Optical Heart Rate Monitor was used to measure heart rate. The Pulse Sensor output was also filtered and amplified using the circuit shown in FIG. 5. Heart rate was determined by measuring the time between the pulses shown in FIG. 6. A FlexiForce® pressure sensor was also implemented in order to detect whether the driver is holding his/her hand on the steering wheel. Just like the Pulse Sensor, the output of this sensor was amplified using the circuit shown in FIG. 7. The output of the amplifier circuit is shown in FIG. 8. Both these sensors were controlled by the FLORA microcontroller (FIG. 1—113) which may be placed behind the airbag in the steering wheel or in the dashboard.

Proximity Subsystem

Materials

The materials used for this subsystem prototype were:
1—LV-EZ1 Ultrasonic sensor (MaxBotix®, Inc.)
2—HB100 Doppler speed sensor (ST Electronics Pte, Ltd.)
3—RPLidar A1M8 360 degree laser scanner (Slamtec. Inc.)

Instrumentation

Simulation for the circuits was accomplished using NI Multisim. Testing and benchmarking was done by constructing the market circuits and obtaining readings using the Arduino software.

Methods

The LIDAR sensor was used to measure long range obstacles, collisions, as well breaking detection. The Doppler sensor was used to measure the speed of a front facing vehicle. The 741 op-amp FIG. 9 was used to amplify the signal of the LIDAR sensor. The ultrasonic sensor is used to detect the blind spot as well as short range obstacles. All the preliminary circuits were constructed on breadboards using jumper wire. Moreover, all sensors were connected to Arduino® microcontrollers. The Arduino® was programmed using the native Arduino® IDE, which utilizes a mixture of C/C++ commands.

Alarm Subsystem

Materials

The materials used for this subsystem prototype were:
1—Vibrating Mini Motor Disc (PLUX—Wireless Biosignals, S.A.)

Methods

When the readings from sensors are at a dangerous level, an alarm signal activates a sensory alert to notify the driver about the situation and prompt appropriate action. An alert is sent as well to the cloud to be processed and the company headquarters will be notified. For example, if the driver is detected to be sleepy, a signal will be sent to the microcontroller which will then trigger the vibrating motor in the steering wheel to alert the driver and wake him up.

Cloud Interface

Materials

The materials used for this subsystem prototype were:
1—WiFi Transceiver ESP8266EX (Shenzhen Anxinke Technology Co.)
2—Google Cloud IoT Service

Methods

A web Application was designed using Ubidots. The application connects all the subsystems together and analyzes the collected data and displays alerts. The data is regularly updated and allowed to be monitored by the trucking company. Both sensors interface with the cloud. The cloud used for the system is Google Cloud IoT which is a complete set of tools to connect, process, store, and analyze data both at the edge and in the cloud. The platform consists of scalable and fully-managed cloud services. The platform receives and processes data from both sensor subsystems. Then it stores the data for the company personnel to monitor. If there are any abnormalities in the collected data, a message will be delivered to the company and to the driver in order to alert him. This will require the cloud to interface with the alarm system as well.

Design Outcomes

Figure 10:
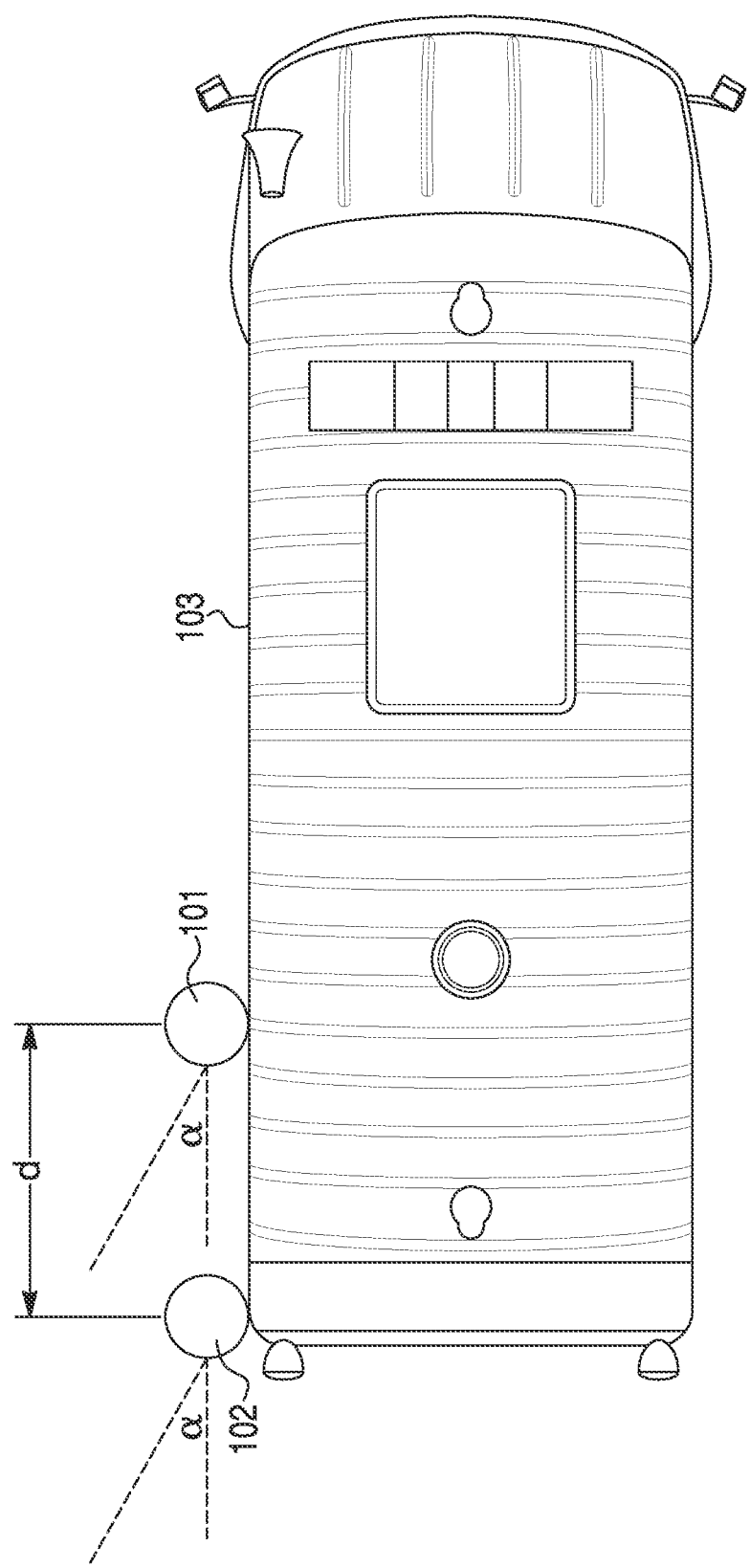
FIG. 10 is a non-limiting diagram showing an exemplary placement of ultrasonic sensors for blind spot detection.

Three sensors were implemented in order to measure distance and velocity. The sensors are an ultrasonic and LIDAR for low range and high range obstacle detection, while velocity is measured using a microwave sensor. The ultrasonic sensors 101 & 102 are used to detect the blind spot of the back of a vehicle 103 (e.g., truck) on both sides. As shown in FIG. 10, two sensors 101 & 102 will be installed on the back side of the vehicle 103. With a known distance between the sensors 101 & 102, the presence of another vehicle (not shown) and relative speed in case $\alpha_1 \leq \alpha_2$ can be detected by knowing the angles of both sensors 101 & 102.

Figure 11:
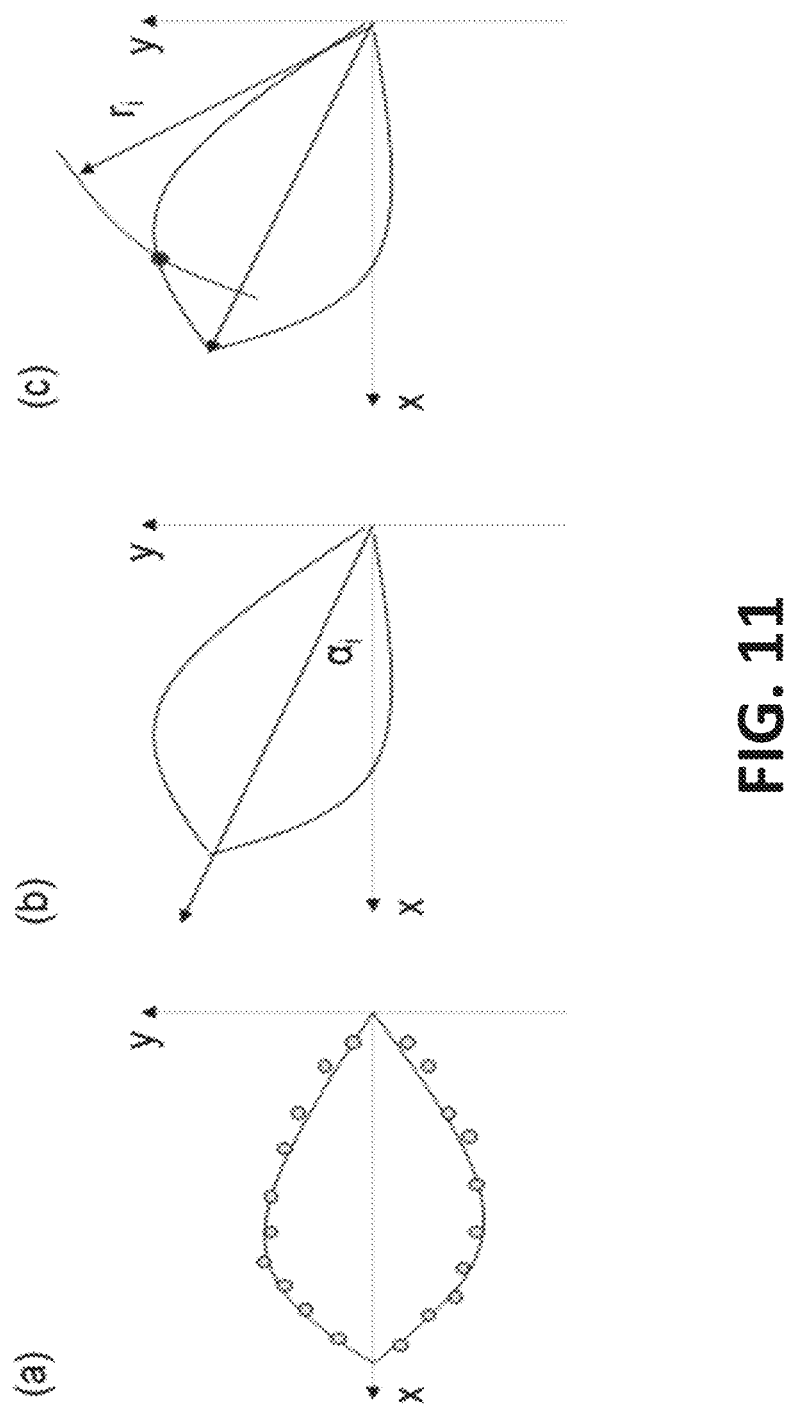
FIG. 11 is a non-limiting diagram showing curve fitting with point of intersection for determining vehicle speed.

In most of the cases vehicles are not parallel and this won't give accurate readings of the speed. Therefore, a second-degree order polynomial as indicated below is required to do curve fitting of the sensor readings and then rotate the curve by an angle $\alpha_i$ as shown in FIG. 11 and with the intersection point of the host vehicle (HV) it will read the relative speed of the other vehicle.

$$y = A*x^2 + B*x$$

$$\begin{bmatrix} x' \\ y' \end{bmatrix} = \begin{bmatrix} \cos\alpha_i & -\sin\alpha_i \\ \sin\alpha_i & \cos\alpha_i \end{bmatrix} \begin{bmatrix} x \\ y \end{bmatrix}$$

$$y' = \frac{-B' \pm \sqrt{B'^2 - 4A'C'}}{2A'}$$

$$A' = A*\sin^2\alpha_i$$

$$B' = 2A*x'\cos\alpha_i \sin\alpha_i + B\sin\alpha_i - \cos\alpha_i$$

$$C' = A*x'^2*\cos^2\alpha_i + B*\cos\alpha_i + x'*\sin\alpha_i$$

Figure 12:
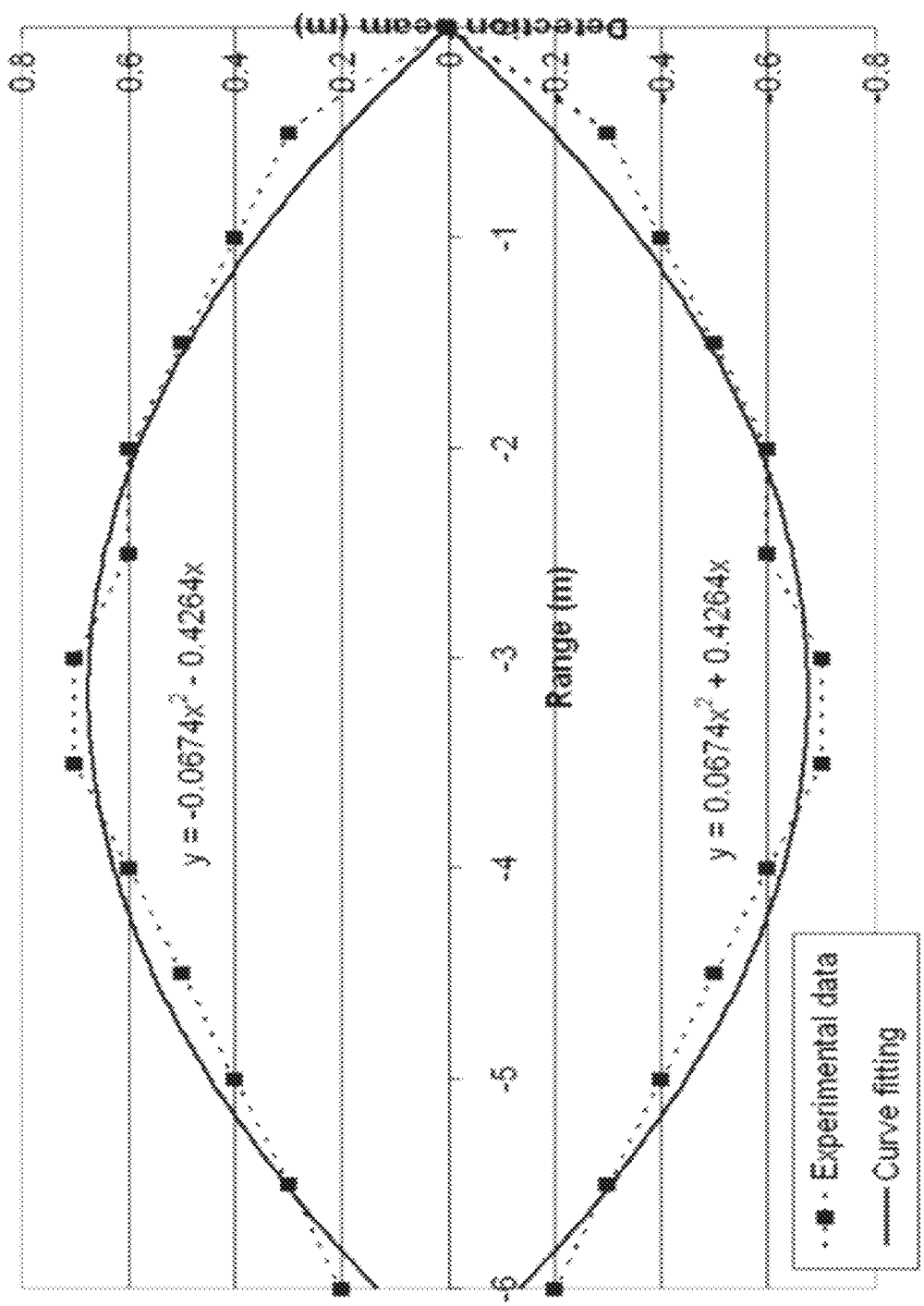
FIG. 12 is a non-limiting diagram showing curve fitting as shown in decay at 6 meters for determining vehicle speed.
Figure 13:
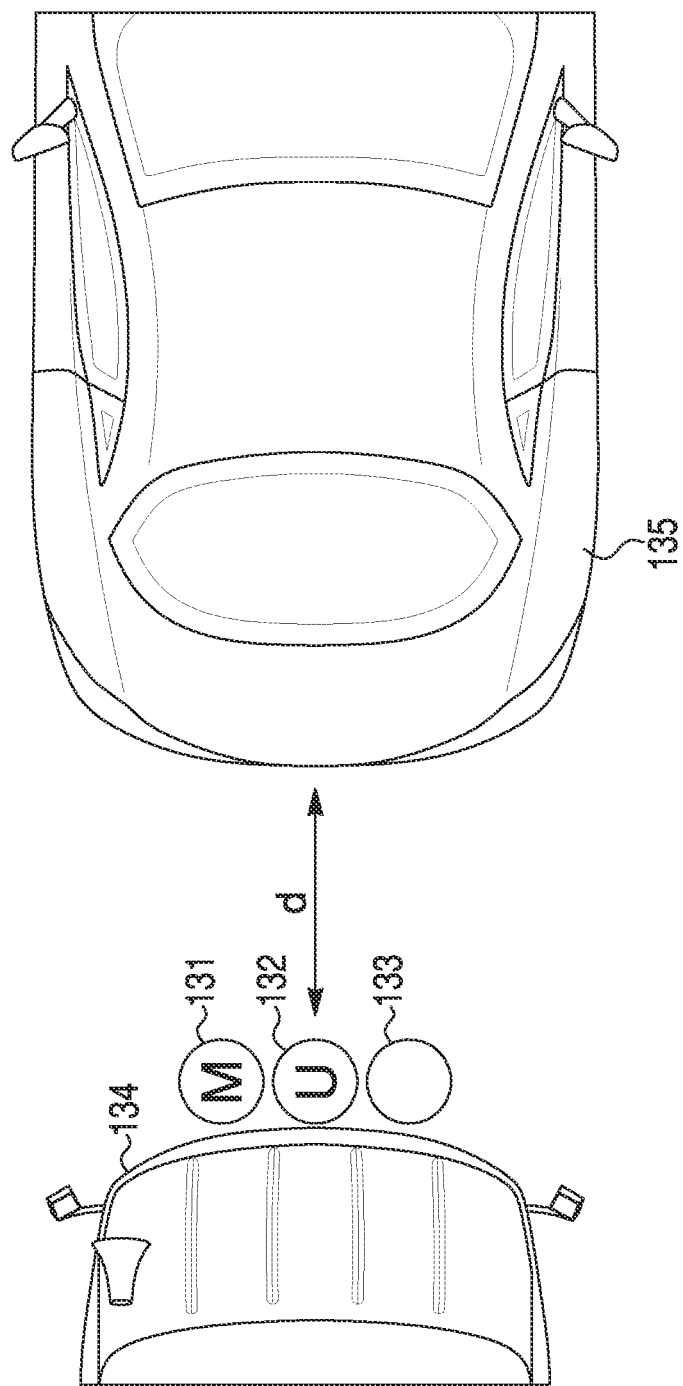
FIG. 13 is a non-limiting diagram showing exemplary placement of ultrasonic sensors on a truck front bumper.
Figure 14:
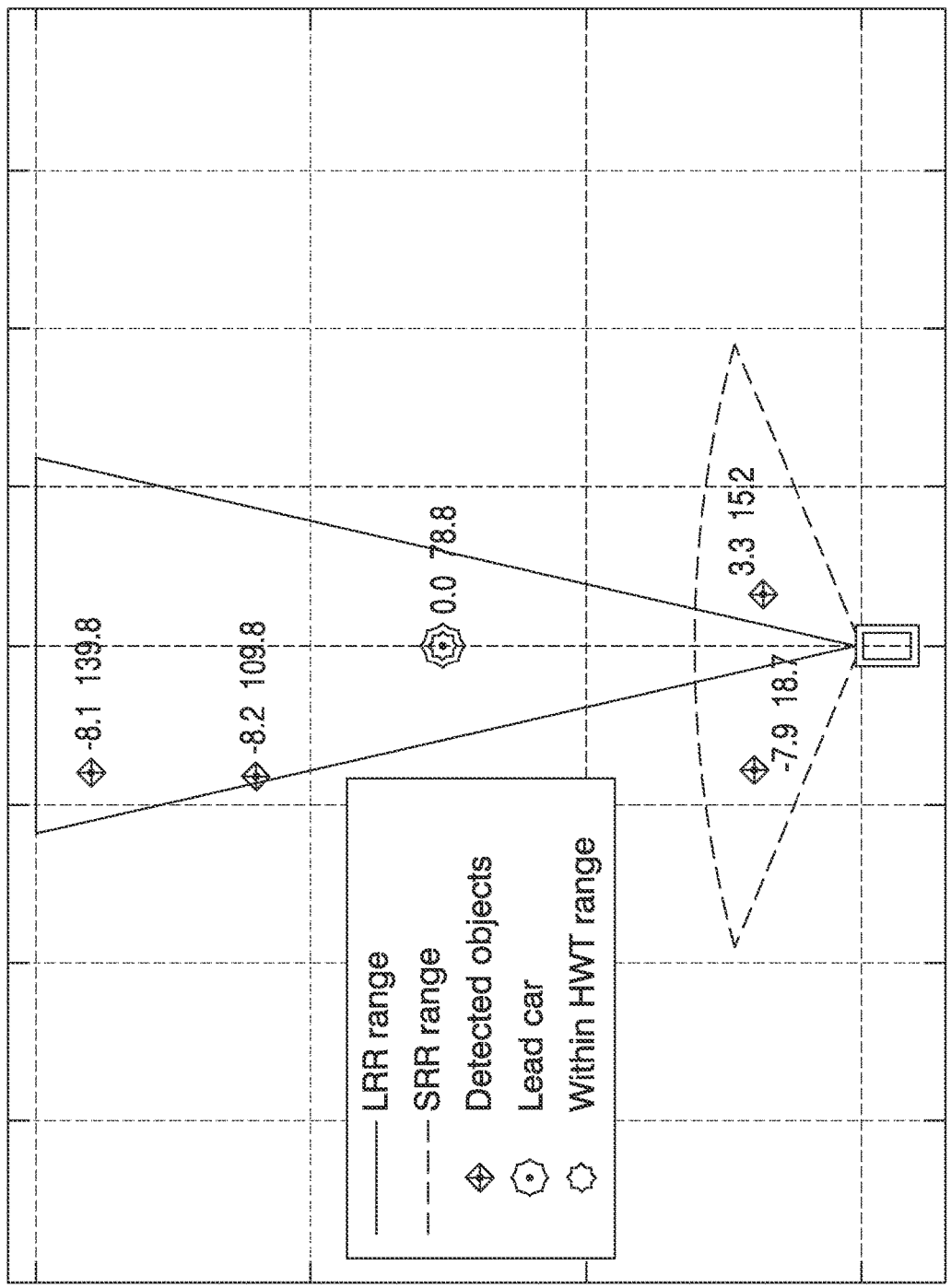
FIG. 14 is a non-limiting diagram showing an obstacle in the range of the vehicle.

In FIG. 12 a collection of the Ultrasonic sensor data with the curve fitting is shown in decay at 6 meters which is the maximum range of sensor detection. For the obstacle detection, three sensors were implemented in the front of a first vehicle 134 (e.g., truck) for obstacles and HV in front of it as shown in FIG. 13. A microwave sensor 131 is used to detect the relative speed between the truck 104 and a front facing vehicle 135. The microwave sensor 131 went through many identifications in the market circuit. The market circuit has no high pass amplifier on the second amplifier and ends up in a high gain of 510 and only 1.96 KHz of bandwidth left inside LM258. The market circuit was modified with the purpose of enhancing the gain of 125.5 and cut off frequency at 3.4 Hz and 999 Hz, which increased the accuracy to starts at 1 Km/h.

The second sensor in the front view shown in FIG. 13 is the ultrasonic sensor 132 which takes readings of the distance with a programmable timer and by taking the difference of distance in terms of time we will have a reading of the velocity. The readings must be accurate to get the best resolution of velocity, as shown in equation [1], as frequency increases the timer will decrease. Accordingly, for the ultrasonic sensor 132 the EZ1 was chosen because of its high frequency of 40 KHz. Therefore, as shown in equation [2] the velocity resolution will increase as the number of cycles between the first and second detection decrease.

Frequency and velocity relation $$\frac{1}{-} = \Delta t \leq \frac{}{v_{ax}} \qquad \text{Equation 1}$$

Number of cycles and velocity resolution $$v = \frac{}{*(+1)*\Delta t} \qquad \text{Equation 2}$$

Thereafter, we detect the acceleration by taking two readings between the first and second velocity reading as shown in [3].

Detect the acceleration $$Aai = \frac{Ep - ap}{i} \qquad \text{Equation 3}$$

Programming wise, three decisions were implemented for the detection algorithms and alert system interrupt services made for the detection algorithm as the declaration start to be between 1 to 5½ it will give a high tone with low frequency and when it gets between 6 to 10½ it will give a high tone with high frequency and when it gets over 10½ it will operate the vibration system in the steering wheel and seat.

The last sensor to be implemented was the LIDAR sensor 133. The LIDAR sensor 133 can detect any obstacles in within an arc of area 25², As shown in the FIG. 14 we can detect the moving obstacles in the range of the vehicle.

The Driver Monitoring System (FIG. 1—100) will be implemented mainly inside the vehicle, with some components (e.g., LIDAR sensors) mounted on external surfaces of the vehicle. Sensors will be installed on the steering wheel. In the prototype, two sensors were implemented: pulse/ECG sensor and an impact/pressure sensor. The first was the pulse/ECG sensor. When the pulse/ECG sensor is interfaced with the Arduino®, the pulse sensor output shown in FIG. 6 is obtained from the corresponding amplification circuit.

Figure 6:
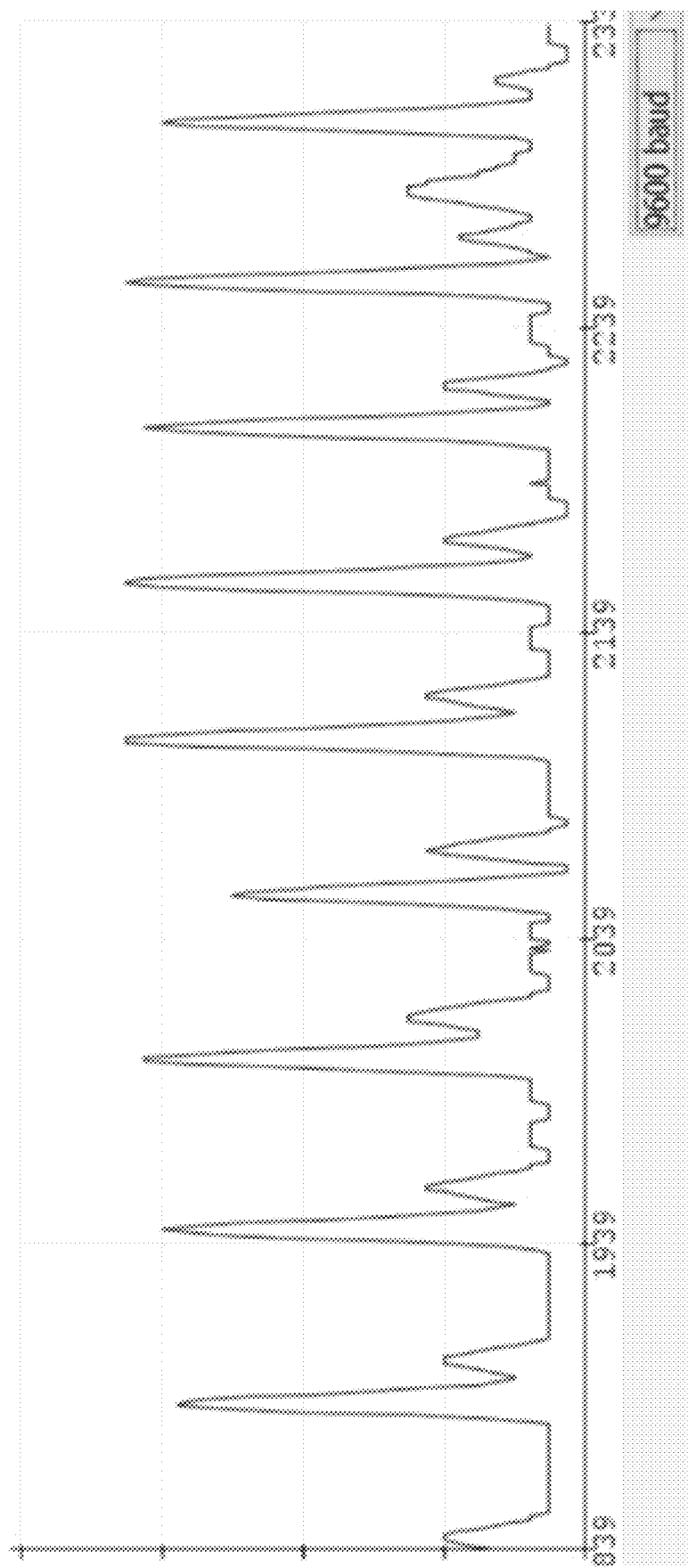
FIG. 6 is a non-limiting diagram showing an exemplary pulse sensor output from the corresponding amplification circuit according to one embodiment of the present invention.
Figure 7:
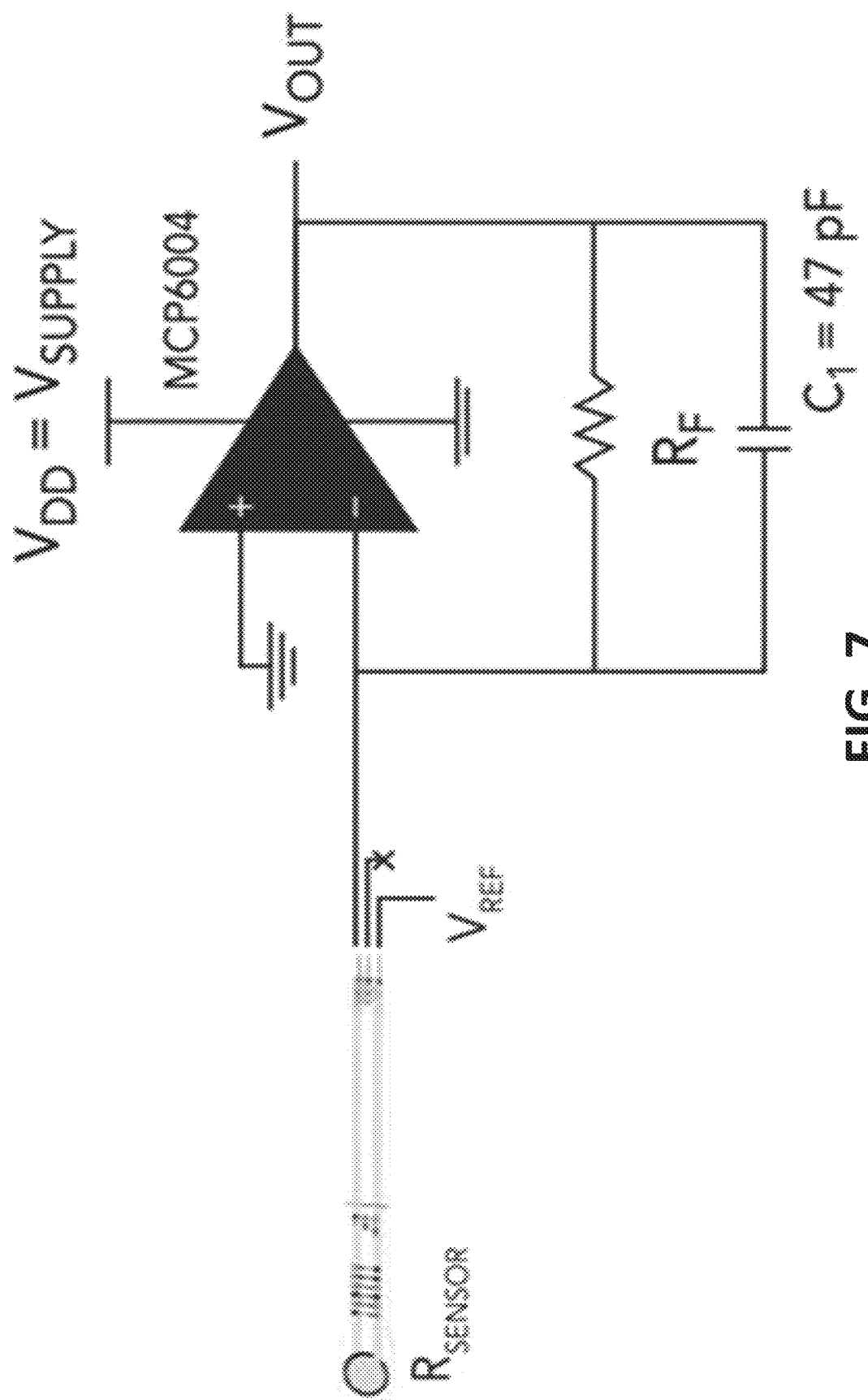
FIG. 7 is a non-limiting diagram schematically showing an exemplary pressure sensor amplification circuit according to one embodiment of the present invention.

As shown in FIG. 6, the produced graphs do represent the shape of heart beat signal. Heart rate may be measured by measuring the period of the wave. The second sensor implemented was a grip sensor that detects whether or not the driver is holding on to the wheel. To detect that, a pressure sensor circuit shown in FIG. 7 was introduced to the system. The results shown in FIG. 8 were obtained. The smaller signals were produced at a softer grip, while the larger signals were produced at a tighter grip, similar to a grip one would typically make when holding a steering wheel.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. A system for detecting abnormal vehicle operation and providing notification and alerts to third parties, comprising:
   an impediment proximity detection subsystem including sensors at least mounted at external surfaces of said vehicle, said impediments consisting of at least fixed and moving objects external to said vehicle;
   a vital sign detection subsystem including driver monitoring sensors and providing a measure of at least driver pulse rate and hand location;
   a controller for receiving and processing sensor produced signals;
   an alarm subsystem producing at least one of a visual or vibrational signal;
   a cloud interface subsystem including at least a WiFi transceiver and a Google Cloud IoT Service or equivalent, and
   a vehicle to vehicle communication subsystem using the BroadR-Reach® standard for automotive Ethernet or its evolving equivalents,
   wherein, said system monitors specific vital signs associated with health conditions of a specific driver, including at least diabetic, high blood pressure, and heart irregularities, and
   wherein, said system monitors specific fatigue profiles of record for said specific driver.

2. The system according to claim 1, wherein said system transmits warning messages to surrounding vehicles, alerting their drivers to avoid a specific motor vehicle in the event of a health or fatigue related negative event.

3. The system according to claim 1, wherein said system is configured to transmit notification said abnormal vehicle operation or driver condition to a remote third party at interest in the event of a health or fatigue related negative event.

4. The system according to claim 3, further comprising a user-interface for receiving and accessing event data.

5. A system for detecting abnormal vehicle operation and providing notification and alerts to third parties, comprising:
   a motor vehicle providing a platform for operation of said system;
   an impediment proximity detection subsystem installed in said motor vehicle, including sensors at least mounted at external surfaces of said motor vehicle, said impediments consisting of at least fixed and moving objects external to said vehicle;
   a vital sign detection subsystem installed in said motor vehicle, including driver monitoring sensors and providing a measure of at least driver pulse rate and hand location;
   a controller installed in said motor vehicle, for receiving and processing sensor produced signals;
   an alarm subsystem installed in said motor vehicle, producing at least one of a visual or vibrational signal;
   a cloud interface subsystem including at least a WiFi transceiver installed in said motor vehicle, and a Google Cloud IoT Service or equivalent, and
   a vehicle to vehicle communication subsystem installed in said motor vehicle, using the BroadR-Reach® standard for automotive Ethernet or its evolving equivalents,
   wherein, said system monitors specific vital signs associated with health conditions of a specific driver, including at least diabetic, high blood pressure, and heart irregularities,
   wherein, said system is monitors specific fatigue profiles of record for said specific driver, and
   wherein, said system is portable and adjustable and can be configured to fit any car or truck.

6. The system according to claim 5, wherein said system transmits warning messages to surrounding vehicles, alerting their drivers to avoid a specific motor vehicle in the event of a health or fatigue related negative event.

7. The system according to claim 5, wherein said system transmits notification of said abnormal vehicle operation or driver condition to a remote third party at interest.

8. The system according to claim 7, further comprising a user-interface for receiving and accessing event data.

9. A method for detecting abnormal vehicle operation and providing notification and alerts to third parties, the method comprising:
   monitoring specific vital signs associated with a specific driver's health conditions, including at least diabetic, high blood pressure, and heart irregularities;
   assessing a specific driver's activity in an operating vehicle against that specific driver's fatigue profile;
   detecting impediment proximity using sensors at least mounted at external surfaces of said vehicle, said impediments consisting of at least fixed and moving objects external to said vehicle;

detecting human vital signs using driver monitoring sensors and measuring at least driver pulse rate and hand location;

receiving and processing sensor produced signals;

producing at least one of a visual or vibrational signal in the event of an abnormal condition;

transmitting event data using a cloud interface subsystem, said subsystem including at least a WiFi transceiver and a Google Cloud IoT Service or equivalent, and transmitting event notifications using a vehicle to vehicle communication subsystem, said subsystem using the BroadR-Reach® standard for automotive Ethernet or its evolving equivalents.

10. The method according to claim 9, wherein said method includes transmission of warning messages to surrounding vehicles, alerting their drivers to avoid a specific motor vehicle in the event of a health or fatigue related negative event.

11. The method according to claim 9, wherein said method includes transmission of notifications to a remote third party at interest providing an alert of said abnormal condition in the event of a health or fatigue related negative event.

12. The method according to claim 11, further comprising implementing a user-interface for receiving and accessing event data.

13. The method of claim 9, further comprising installing in a motor vehicle, said driver monitoring sensors and a controller for receiving and processing signals from said driver monitoring sensors.

14. The method of claim 13, further comprising installing impediment proximity sensors.

15. The method of claim 9, further comprising receiving and accessing notification of said abnormal condition.

\* \* \* \* \*